United States Patent [19]
Dowd et al.

[11] 4,014,880
[45] Mar. 29, 1977

[54] PROCESS FOR MAKING IMIDAZOLINES AND TETRAHYDROPYRIMIDINES FROM OXAZOLINES AND ALKYLENEDIAMINES

[75] Inventors: William Dowd; Peter W. Owen, both of Midland, Mich.

[73] Assignee: The Dow Chemical Company, Midland, Mich.

[22] Filed: Feb. 9, 1976

[21] Appl. No.: 656,558

[52] U.S. Cl. .................. 260/251 R; 260/309.7; 260/307 F
[51] Int. Cl.² ................................. C07D 239/00
[58] Field of Search .................. 260/251 R, 309.7

[56] References Cited
FOREIGN PATENTS OR APPLICATIONS
2,154,948  11/1971  Germany ................. 260/251 R OTHER PUBLICATIONS
Chem. Abst. 76, 113164u (1972).

*Primary Examiner*—Lewis Gotts
*Assistant Examiner*—D. R. Phillips
*Attorney, Agent, or Firm*—L. Wayne White

[57] ABSTRACT

The reaction of 2-oxazolines with 1,2- or 1,3-alkylenediamines to form 2-imidazolines or 1,4,5,6-tetrahydropyrimidines is catalyzed by Lewis acids.

9 Claims, No Drawings

PROCESS FOR MAKING IMIDAZOLINES AND TETRAHYDROPYRIMIDINES FROM OXAZOLINES AND ALKYLENEDIAMINES

BACKGROUND OF THE INVENTION

The 2-imidazolines and 1,4,5,6tetrahydropyrimidines are known classes of compounds having many members and many utilities. Such compounds, or derivatives thereof, are commercially marketed as amphoteric surfactants, as corrosion inhibitors in the oil industry, and have even been examined as analgesics.

There are relatively few methods of preparing 2-imidazolines and 1,4,5,6-tetrahydropyrimidines described in the open literature. Those methods that are described range from a fairly crude "cooking" process of carboxylic acids and diamines to the process involving the reaction of nitriles with diamines. The latter process produces the imidazolines in high yields and high purity but is limited by the cost and availability of many nitriles. These and other methods of preparing imidazolines are described in a review article by R. J. Ferm and J. L. Riebsomer, *Chemical Reviews*, 54, 593–613 (1954).

Another method of preparing 2-imidazolines and 1,4,5,6-tetrahydropyrimidines comprises reacting a 2-oxazoline with a 1,2- or a 1,3-alkylenediamine. This method was reported by K. H. Magosch, *Synthesis* 1972, No. 1, 37 (1972). Crude yields varied from 60–61 percent for the imidazolines and varied from 19–73 percent for the tetrahydropyrimidines. The reactions were conducted by merely blending the reactants together and heating the mixture at a temperature of from about 180° to 200° C for periods of up to 10 hours.

SUMMARY OF THE INVENTION

We have discovered that the reaction of 2-oxazolines with 1,2- or 1,3-alkylenediamines to form the corresponding 2-imidazolines or 1,4,5,6tetraydropyrimidines is catalyzed by Lewis acids.

DETAILED DESCRIPTION OF THE INVENTION

The reactants and catalysts in this process are known classes of compounds.

The 2-oxazolines are described, for example, by: J. A. Frump, *Chemical Reviews*, 1971, Vol. 71, No. 5, 483 (1971); W. Seeliger et al., *Angew. Chem. Internat. Edit.*, Vol. 5, No. 10, 875 (1966); R. H. Wiley et al., *Chemical Reviews*, Vol. 44, 447 (1949); and are generally classified in the classification manual of the U.S. Patent and Trademark Office under 260–307 F. Any member of this known class of compounds may be used in the instant invention but the preferred reactants are those corresponding to formula I below:

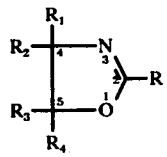

wherein R is alkyl, aryl or inertly-substituted alkyl or aryl; and $R_1$–$R_4$ are each independently hydrogen, lower alkyl or hydroxy-substituted lower alkyl. By "lower alkyl" is meant alkyl groups of 1 to 4 carbon atoms. The term "inertly-substituted" is meant to denote any substituent which is inert in the instant process. The term thus includes hydroxyl groups, halo groups, etc. The most preferred reactants are presented by formula I wherein R is alkyl of from 1 to about 20 carbon atoms and $R_1$–$R_4$ are each hydrogen.

Representative examples of the known class of oxazolines include, for example, 2-methyl-, 2-ethyl-, 2-propyl-, 2-heptyl-, 2-nonyl-, 2-heptadecyl-, 2-phenyl-, 2-tolyl-, 2-butylphenyl-, 2-chlorophenyl-, 2-hydroxyphenyl-, 2-α-(hydroxymethyl)ethyl-2-oxazoline and the corresponding 4-methyl-, 4,4-dimethyl-, 4-butyl-, 5-methyl-, 4-hydroxymethyl-, 4,4-bis-hydroxymethyl-2-oxazolines, and the like.

The 1,2- and 1,3-alkylenediamines here used are likewise a known class of compounds. The preferred compounds are represented by formula II:

$$R_5-NH-CHR_6 \text{\small(} \quad\quad\quad\quad\quad II$$

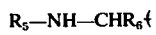

wherein $R_5$ is hydrogen, lower alkyl or inertly-substituted lower alkyl of 1 to 4 carbon atoms (e.g. benzyl, phenethyl, hydroxyethyl, etc.); $R_6$ is hydrogen or lower alkyl of 1 to 4 carbon atoms (e.g. methyl, ethyl, propyl, butyl); and n is 1 or 2. The most preferred reactants are those described by II wherein $R_5$ is hydrogen and $R_6$ is hydrogen, methyl or ethyl. Further, the 1,2-ethylenediamine reactants are preferred over the 1,3-propylenediamine reactants based on commercial availability and cost.

Representative examples of the alkylenediamine reactants include ethylenediamine, N-methylethylenediamine, N-ethylethylenediamine, N-butylethylenediamine, N-hexylethylenedimine, N-benzylethylenediamine, N-hydroxyethylethylenediamine, and the corresponding 1,2- and 1,3-propylenediamines, and the like.

The Lewis acids, which are here used as catalysts, also form a known class of compounds having many members. See, for example, Satchell et al., *Chemical Reviews*, Vol. 69, No. 3, 251–278 (1969). Any member of this class of compounds may be used herein. Representative compounds from this class of compounds include, for example, the halides of boron, aluminum, iron, tin, zinc, gallium, antimony, phosphorus, titanium, nickel, etc. (e.g. $BF_3$ etherate, $AlCl_3$, $AlBr_3$, $FeCl_3$, $SnCl_3$, $SnBr_4$, $ZnCl_2$, $GaCl_3$.etherate, $GaBr_3$.etherate, $SbF_5$, $SbCl_5$, $PCl_3$, $PBr_3$, $TiCl_4$, and the like); alkyl derivatives of boron, aluminum, tin, etc. (e.g. trimethyl-boron, trimethyl-aluminum, triethylaluminum, methyltin trichloride, n-butyltin trichloride, phenyltin trichloride, and the like), and other like inorganic and organometallic Lewis acids.

The reaction is conducted by blending the reactants (normally in an essentially stoichiometric amount) and catalyst and warming the reaction mixture at a temperature sufficient to promote an exotherm. Normally, the rate of reaction is quite satisfactory at reaction temperatures of from about 70° to about 130 ° C. The reaction may be conducted neat or in an inert solvent (e.g. toluene, xylene, perchloroethylene, etc). The reaction yield is further enhanced by conducting the reaction under anhydrous or substantially anhydrous conditions. The oxazoline reactant is susceptible to hydrolysis at elevated temperatures and water can result in the lowering of product yield.

EXPERIMENTAL

The following experiments will further illustrate the invention.

EXAMPLES 1-6

These reactions were conducted by blending the desired oxazoline, alkylenediamine and catalyst as indicated in Table 1 below in a reaction flask at room temperature. The flask was equipped with a heating means, a stirring means, and a reflux condenser. The reaction mixture was warmed to 100° C and a zero time sample withdrawn. The reaction mixture was maintained at 100° C for 2 hours and the 2-imidazoline product recovered therefrom by distillation under reduced pressure or by recrystallization.

The distillations were carried out on a 1-inch (inside diameter) vacuum jacketed 5-plate Odlershaw column. Distillations were conducted at 10-20 mm of pressure.

The recrystallizations were conducted using methanol as the medium. Initial crops of crystals were collected using 3-5 ml of methanol per gram of crude reaction product. Subsequent crops of crystals were collected by stripping methanol from the filtrate. The percent yield was calculated using the combined crops of crystals. In Experiments 1-5, zinc acetate dihydrate ($Zn(OAc)_2 \cdot 2H_2O$) was added as the catalyst in an amount of 0.5 mole percent. The 2-oxazoline and alkylenediamine reactants were added in equimolar amounts.

TABLE 1

$$\underset{\substack{R_1 \\ H}}{\square}\!\!\!\!\!\!\!\!\!\!\!\!\!\!\!\overset{N}{\underset{O}{\diagdown}}\!\!\!\!-R \;+\; R_5-NH-(CH_2)_m-NH_2 \;\longrightarrow$$

$$(CH_2)_m\!\!\!\!\overset{N}{\underset{\underset{R_5}{N}}{\diagdown}}\!\!\!\!-R \;+\; NH_2CH_2CHR_1OH$$

| Ex. | R | $R_1$ | $R_5$ | m | Yield (%) |
|---|---|---|---|---|---|
| 1 | $C_2H_5$ | H | H | 2 | 87 |
| 2 | $CH_3$ | $CH_3$ | H | 2 | 88 |
| 3 | $CH_3$ | $CH_3$ | H | 3 | 84 |
| 4 | $CH_3$ | $CH_3$ | $C_2H_4OH$ | 2 | 86 |
| 5 | $C_{11}H_{23}$ | H | H | 2 | 90 |
| *6 | $C_2H_5$ | H | H | 2 | 79 |

*Experiment 6 contained no catalyst and represents a "blank".

The reaction products from Examples 2 and 5 were recovered by recrystallization and the remainder of the products were recovered by distillation.

EXAMPLES 7-14

In a separate series of experiments, 2-ethyl-2-imidazoline was prepared by reacting 2-ethyl-2-oxazoline with 1,2-ethylenediamine on a 0.2 mole scale for each reactant using 0.05 mole percent of the catalyst as indicated in Table 2 below. In this series of experiments, the oxazoline reactant and catalyst were charged to a 100 ml 3-necked flask equipped with a magnetic stirrer, heating means, condenser, and temperature recording means. The mixture of oxazoline and catalyst was heated to 90° C and the ethylenediamine reactant (preheated to 90° C) was added to the reaction vessel through the condenser. A sample was taken immediately after the diamine was added and subsequent samples were taken to follow the reaction. The reaction mixture was maintained at 90° C for 90 minutes after blending of the reactants and the reaction mixture then analyzed by gas-phase chromatography to determine percent conversion of 2-ethyl-2-oxazoline and the percent yield of 2-ethyl-2-imidazoline based on the converted 2-ethyl-2-oxazoline. The results are summarized in Table 2 below.

TABLE 2

| Ex. | Catalyst | Oxazoline Conversion(%) | Product Yield(%) |
|---|---|---|---|
| 7 | $CrCl_2 \cdot 6H_2O$ | 94.0 | 97.7 |
| 8 | $MoO_2$ | 80.6 | 83.5 |
| 9 | $H_2WO_3$ | 95.6 | 100.0 |
| 10 | $Zn(OAc)_2 \cdot 2H_2O$ | 88.7 | 92.0 |
| 11 | $CdCl_2 \cdot 2.5H_2O$ | 84.5 | 87.5 |
| 12 | $HgCl_2$ | 94.8 | 95.0 |
| 13 | $AlCl_3$ | 93.1 | 97.5 |
| 14 | none | 74.5 | 77.2 |

The catalyst used in Examples 8 and 9 were partially insoluble throughout the course of the reaction. The catalyst used in Example 11 was partially insoluble for approximately 15 minutes after the ethylenediamine reactant was added. The catalyst in Example 13 was insoluble in the oxazoline reaction but went into solution during the course of the reaction. The remaining catalysts were soluble in the reaction mixture.

EXAMPLES 15-16

In a similar manner, 2-methyl-2-imidazoline was prepared in two experiments by reacting stoichiometric amounts of 2-methyl-2-oxazoline with 1,2-ethylenediamine on a 0.2 mole scale in the presence of a catalytic amount of zinc chloride (Ex. 15) and zinc acetate dihydrate (Ex. 16).

The above examples are merely illustrative and other Lewis acids could be similarly used in the above combination reactants or other combinations of reactants to produce the desired 2-imidazoline or 1,4,5,6-tetrahydropyrimidine products.

We claim:

1. In the method of preparing a 2-imidazoline or a 1,4,5,6-tetrahydropyrimidine by reacting (a) a 2-oxazoline with (b) 1,2-alkylenediamine or a 1,3-alkylenediamine in liquid-phase, the improvement comprising conducting the reaction in the presence of a small but sufficient amount of a Lewis acid to catalyze the reaction between (a) and (b).

2. The process defined by claim 1 wherein the oxazoline reactant is of the formula

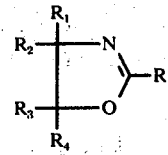

wherein R is alkyl, aryl, or inertly-substituted alkyl or aryl and $R_1$-$R_4$ are each independently hydrogen, lower alkyl or hydroxy-substituted lower alkyl.

3. The process defined by claim 2 wherein R is alkyl of from 1 to about 20 carbon atoms and $R_1$-$R_4$ are each hydrogen.

4. The process defined by claim 1 wherein reactant (b) is of the formula

wherein $R_5$ is hydrogen, lower alkyl or inertly-substituted lower alkyl; $R_6$ is hydrogen or lower alkyl; and n is 1 or 2.

5. The process defined by claim 4 wherein $R_5$ is hydrogen and $R_6$ is hydrogen, methyl or ethyl.

6. The process defined by claim 4 wherein n is 1.

7. The process defined by claim 1 wherein the catalyst is of the formula

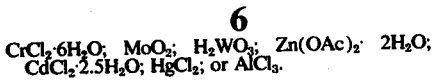

8. The process defined by claim 7 wherein (a) is 2-ethyl-2-oxazoline and (b) is 1,2-ethylenediamine or 1,3-propylenediamine.

9. The process defined by claim 1 wherein (a) is 2-methyl-2-oxazoline, 2-ethyl-2-oxazoline, 2,5-dimethyl-2-oxazoline, or 2-undecyl-2oxazoline (b) is 1,2-ethylenediamine, 1,3-propylenediamine or N-hydroxyethyl ethylenediamine and the Lewis acid catalyst is zinc acetate dihydrate.

* * * * *

UNITED STATES PATENT AND TRADEMARK OFFICE
CERTIFICATE OF CORRECTION

PATENT NO. : 4,014,880

DATED : March 29, 1977

INVENTOR(S) : William Dowd and Peter W. Owen

It is certified that error appears in the above-identified patent and that said Letters Patent are hereby corrected as shown below:

Column 1, line 7: "1,4,5,6tetrahydropyrimidines" should read --1,4,5,6-tetrahydropyrimidines--.

Column 1, lines 40 and 41: "1,4,5,6tetraydropyrimidines" should read --1,4,5,6-tetrahydropyrimidines--.

Column 1, line 60: Roman Numeral --I-- should be inserted before the formula.

Column 2, line 20: "$R_5-NH-CHR_6\{$" should read --$R_5-NH-CHR_6(CH_2)_nNH_2$--.

Column 2, line 22: "hyd$^{CH_2)_n NH_2}$ower" should read --hydrogen, lower--.

Column 2, line 35: "N-hexylethylenedimine," should read --N-hexylethylenediamine,--.

Column 2, line 48: "$SnCl_3$," should read --$SnCl_4$;--.

Column 6, line 9, Claim 9, line 3: "2-undecyl-2oxazoline" should read --2-undecyl-2-oxazoline;--.

Signed and Sealed this twenty-sixth Day of July 1977

[SEAL]

Attest:

RUTH C. MASON
*Attesting Officer*

C. MARSHALL DANN
*Commissioner of Patents and Trademarks*